United States Patent [19]

van Andel

[11] Patent Number: Plant 6,865

[45] Date of Patent: Jun. 20, 1989

[54] ALSTROEMERIA NAMED STAROVER

[75] Inventor: Jacob van Andel, Aalsmeer, Netherlands

[73] Assignee: Van Staaveren, B.V., Aalsmeer, Netherlands

[21] Appl. No.: 93,875

[22] Filed: Sep. 4, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new and distinct variety of Alstroemeria particularly distinguished by the very large size of its blossoms, the outer petals of which are of an oval shape with light pink-white and purple coloration contrasted by the yellow and heavily striped inside petals, which provides an unusual and attractive floral appearance, the blossoms being borne singly on the strong stems of an umbel formation carried at the top of a tall, straight and strong main stem.

1 Drawing Sheet

BACKGROUND OF THE NEW PLANT

This new Alstroemeria cultivar originated as a sport of the variety 'Staronic' growing in greenhouse at Aalsmeer, Holland, and because of the large size of the blooms, the oval shape of their petals, and their attractive color distribution, this sport was asexually reproduced by me and under my direction at Aalsmeer in 1986 by its own root and further propagation through several generations, by dividing rhizomes, has demonstrated that the novel characteristics of the new plant hold true from generation to generation and appear to be firmly fixed.

DESCRIPTION OF THE DRAWING

This new Alstroemeria plant is illustrated by the accompanying photographic drawing which shows a plurality of its blossoms in face view and full color together with buds in various stages of maturity and illustrates the flower formation and coloration, the colors shown being as nearly true to those specified herein as is reasonably possible to obtain by professional photographic procedures.

DESCRIPTION OF THE NEW PLANT

The following is a detailed description of my new Alstroemeria cultivar based upon observations of greenhouse grown plants made in 1987 at Aalsmeer, Holland, the color designations being specified according to The R.H.S. Colour Chart published by The Royal Horticultural Society at London, England.

THE PLANT

Origin: Sport.
Parentage: The variety named 'Staronic'.
Classification:
- *Botanic.*—Alstroemeria.
- *Commercial.*—Alstroemeria Clone.

Form: Tall, erect bush.
Height: About 200 cm.
Main stem length: About 150 to 200 cm., depending upon season.
Growth habit: Vigorous, strong and upright.
Foliage:
- *Quantity.*—Medium.

- *Number of leaves.*—Depending upon season.
- *Size of leaf.*—Various, increasing during season.
- *Shape.*—Elliptic with entire margins.
- *Texture.*—Leathery.
- *Color.*—Upper side — Middle Green. Under side — Middle Grey/Green.

Rhizomes:
- *Size.*—Depending on season and age of plant.
- *Color.*—White.

THE BUD

Size: Large.
- *Diameter.*—About 1.5 cm.
- *Length.*—About 4 cm.

Form: Pear shaped.
Color: When petals begin to unfurl, 67 C.
Sepals:
- *Number.*—Five.
- *Shape.*—Normal. The sepals are hooded over the bud until they divide and when the flowers open, the sepals curl back.

Calyx:
- *Shape.*—Pear shaped.
- *Size.*—Large.
- *Splitting.*—The calyx does not split.
- *Aspect.*—Smooth.

THE FLOWER

Blooming habit: Continuous and profuse throughout the year.
Size of bloom: Very large.
- *Diameter.*—About 6 cm.
- *Depth.*—About 5 cm.

Borne: Singly on the stems of an umbel formation.
Shape: When bloom matures, funnel-like with the petal tips curling outward.
Petalage:
- *Number of petals.*—Six.
- *Shape.*—Oval outer petals; elliptical inner petals.
- *Arrangement.*—Two concentric groups of three.
- *Texture.*—Leathery.
- *Aspect.*—Shiny.
- *Color.*—Outer petals — Generally 67 C with whitish-pink margins. Inside petals — Uppermost pair: Body, Yellow, 12 B, with outer ends generally 67 C; the lower petal is generally white, and all inside petals are heavily marked with longitudinally extending, dark purple stripes from the base to the petal tip.

Peduncle:

*Length.*—1 cm.

*Color.*—Middle Green.

Persistence: The flowers hang on and dry.

Lasting quality: On the plant, about twenty-one days. As a cut flower, about fifteen days in vase keeping.

THE REPRODUCTIVE ORGANS

Stamens:

*Number.*—Six.

*Arrangement.*—One opposite each petal.

*Anthers.*—Size: About 6 mm. Color: Grey/Green.

*Filaments.*—Length: About 4.5 cm. Color: Light Pink.

*Pollen.*—Color: Dark Blue/Grey.

*Pistils.*—Number: One.

Style:

*Length.*—4 to 6 cm.

*Color.*—Pink/White.

*Stigma.*—Color: Pink.

Characteristics of ovary: Normal.

FRUIT

Fertility: The fruit is fertile.

Shape: Capsular.

Color at maturity: Light brown.

This new Alstroemeria variety most nearly resembles its parent 'Staronic' but differs in flower coloring, petal marking and shape, as well as wintertime flower production. Moreover, this new variety is less susceptible to flower bud desiccation as compared with 'Staronic' and the plant is of lower height during winter growing.

I claim:

1. The new and distinct Alstroemeria variety and the parts thereof, substantially as herein shown and described, characterized by the large size and the light purple and yellow coloration of the flowers, which are borne singly on strong stems of an umbel formation carried by a strong, tall stem.

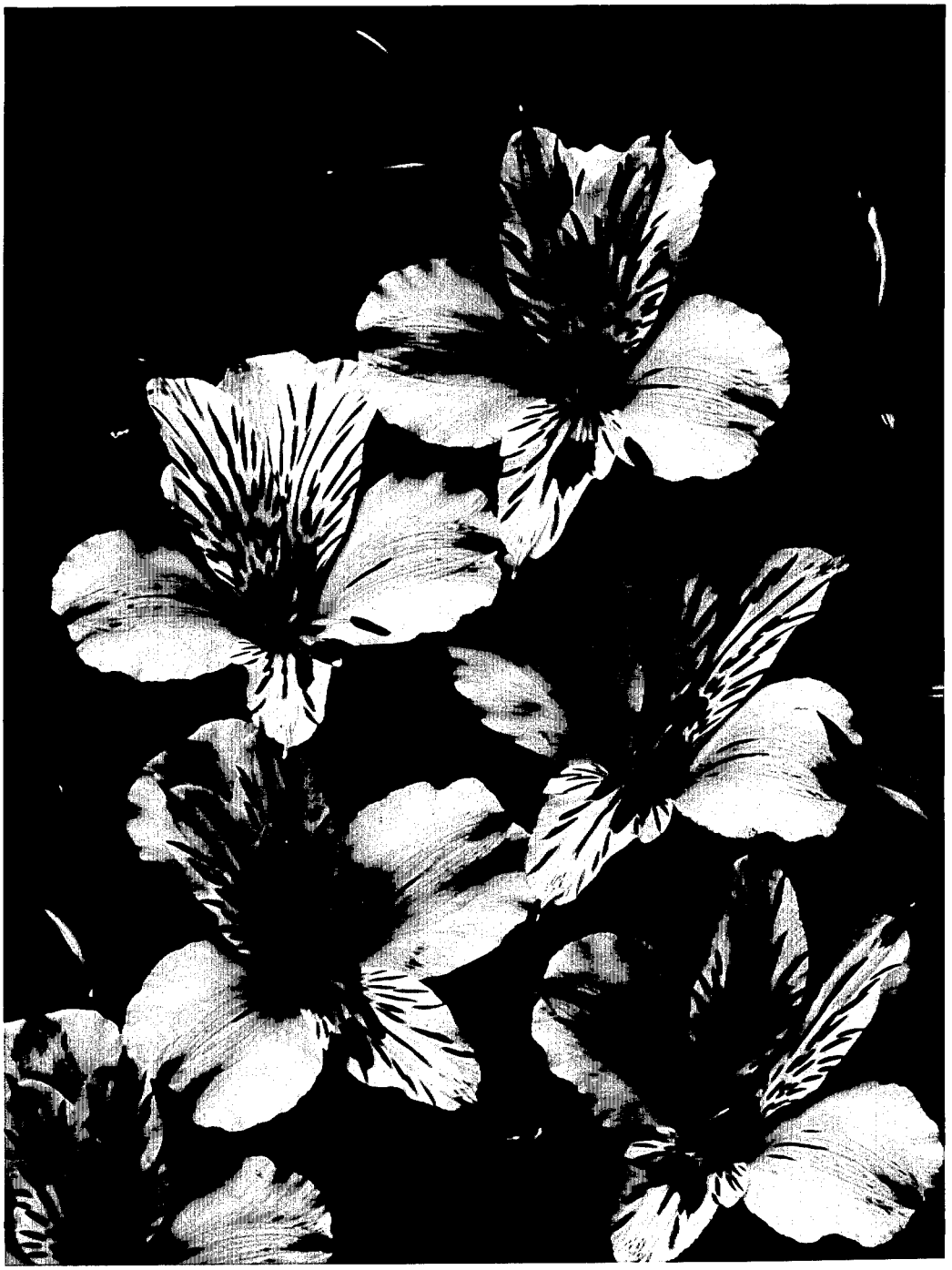

* * * * *